US012803049B2

(12) United States Patent
Kim et al.

(10) Patent No.: US 12,803,049 B2
(45) Date of Patent: Nov. 17, 2026

(54) NON-AQUEOUS ELECTROLYTE SOLUTION ADDITIVE FOR LITHIUM SECONDARY BATTERY, AND NON-AQUEOUS ELECTROLYTE SOLUTION FOR LITHIUM SECONDARY BATTERY AND LITHIUM SECONDARY BATTERY WHICH INCLUDE THE SAME

(71) Applicants: LG Chem, Ltd., Seoul (KR); LG Energy Solution, Ltd., Seoul (KR)

(72) Inventors: Su Jeong Kim, Daejeon (KR); Jeong Ae Yoon, Daejeon (KR); Jung Min Lee, Daejeon (KR); Mi Sook Lee, Daejeon (KR); Won Kyun Lee, Daejeon (KR); Duk Hun Jang, Daejeon (KR); Chan Woo Noh, Daejeon (KR); Chul Eun Yeom, Daejeon (KR); Kyoung Hoon Kim, Daejeon (KR); Chul Haeng Lee, Daejeon (KR)

(73) Assignees: LG Chem, Ltd., Seoul (KR); LG Energy Solution, Ltd., Seoul (KR)

( * ) Notice: Subject to any disclaimer, the term of this patent is extended or adjusted under 35 U.S.C. 154(b) by 747 days.

(21) Appl. No.: 18/031,991

(22) PCT Filed: Mar. 28, 2022

(86) PCT No.: PCT/KR2022/004349

§ 371 (c)(1),
(2) Date: Apr. 14, 2023

(87) PCT Pub. No.: WO2022/211425

PCT Pub. Date: Oct. 6, 2022

(65) Prior Publication Data

US 2024/0014443 A1 Jan. 11, 2024

(30) Foreign Application Priority Data

Mar. 29, 2021 (KR) ........................ 10-2021-0040213

(51) Int. Cl.
*H01M 10/0567* (2010.01)
*C07D 327/04* (2006.01)
*C07D 411/12* (2006.01)
*H01M 10/0525* (2010.01)

(52) U.S. Cl.
CPC ...... *H01M 10/0567* (2013.01); *C07D 327/04* (2013.01); *C07D 411/12* (2013.01); *H01M 10/0525* (2013.01); *H01M 2300/0025* (2013.01)

(58) Field of Classification Search
None
See application file for complete search history.

(56) References Cited

U.S. PATENT DOCUMENTS

| | | | |
|---|---|---|---|
| 2013/0004862 | A1 | 1/2013 | Miyoshi et al. |
| 2013/0171514 | A1 | 7/2013 | Mio et al. |
| 2014/0093787 | A1 | 4/2014 | Abe et al. |
| 2015/0270575 | A1 | 9/2015 | Nishie et al. |
| 2015/0280282 | A1 | 10/2015 | Nishie et al. |
| 2020/0313237 | A1 | 10/2020 | Hu et al. |
| 2024/0097187 | A1 | 3/2024 | Qian et al. |

FOREIGN PATENT DOCUMENTS

| | | | |
|---|---|---|---|
| CN | 109950621 | A | 6/2019 |
| CN | 112047921 | A | 12/2020 |
| EP | 2704246 | A1 | 3/2014 |
| EP | 2905836 | A1 | 8/2015 |
| EP | 2913880 | A1 | 9/2015 |
| EP | 3731325 | A1 | 10/2020 |
| EP | 4273962 | A1 | 11/2023 |
| JP | 6225914 | B2 | 11/2017 |
| JP | 2018156761 | A | 10/2018 |
| JP | 2019179638 | A | 10/2019 |
| KR | 20130043221 | A | 4/2013 |
| KR | 20140031233 | A | 3/2014 |
| WO | 2011122449 | A1 | 10/2011 |
| WO | 2012053644 | A1 | 4/2012 |
| WO | 2012147818 | A1 | 11/2012 |
| WO | 2014054197 | A1 | 4/2014 |
| WO | 2014068805 | A1 | 5/2014 |
| WO | 2019119765 | A1 | 6/2019 |

OTHER PUBLICATIONS

Database Registry, 2008, RN 1005104-25-5, Retrieved from STN international [online]; retrieved on Mar. 6, 2024, 1 page.
Extended European Search Report including Written Opinion for Application No. 22781544.6 dated Mar. 19, 2024, pp. 1-9.
Search report from International Application No. PCT/KR2022/004349, mailed Jun. 30, 2022.

*Primary Examiner* — Carlos Barcena
(74) *Attorney, Agent, or Firm* — Lerner David LLP

(57) ABSTRACT

The present invention relates to a compound having a cyclic sulfur oxide structure, and a non-aqueous electrolyte solution additive, a non-aqueous electrolyte solution, and a lithium secondary battery which include the same, wherein the lithium secondary battery of the present invention may achieve improved effects in terms of high-temperature stability and gas generation while being able to achieve stable performance for a long time.

11 Claims, No Drawings

NON-AQUEOUS ELECTROLYTE SOLUTION ADDITIVE FOR LITHIUM SECONDARY BATTERY, AND NON-AQUEOUS ELECTROLYTE SOLUTION FOR LITHIUM SECONDARY BATTERY AND LITHIUM SECONDARY BATTERY WHICH INCLUDE THE SAME

CROSS-REFERENCE TO RELATED APPLICATIONS

The present application is a national stage entry under U.S.C. § 371 of International Application No. PCT/KR2022/004349 filed on Mar. 28, 2022, which claims priority from Korean Patent Application No. 10-2021-0040213 filed on Mar. 29, 2021, all the disclosures of which are incorporated herein by reference.

TECHNICAL FIELD

The present invention relates to a compound capable of providing excellent high-temperature cycle characteristics and high-temperature storage characteristics when used as a non-aqueous electrolyte solution additive, and a non-aqueous electrolyte solution and a lithium secondary battery which include the same.

BACKGROUND ART

Lithium secondary batteries are the most popular energy storage devices in recent years because they may store high-density energy while being able to be miniaturized and lightweight. The lithium secondary batteries are being used in products in various fields, from small portable devices, such as mobile phones and notebooks, to large devices such as electric vehicles, and, since environments or conditions in which each product is used are different, it is important to achieve stable performance regardless of the environments and conditions.

The lithium secondary battery largely includes a positive electrode, a negative electrode, a separator, and an electrolyte solution. The positive electrode is a source of lithium ions, wherein the lithium ions of the positive electrode move to the negative electrode and are stored during charge, and the lithium ions stored in the negative electrode emit electrons in a process of moving to the positive electrode during discharge to generate electrical energy. The electrolyte solution acts as a medium for the lithium ions to be able to move between the positive electrode and the negative electrode, and includes a salt, a solvent, and an additive. The salt acts as a movement path for the lithium ions, the solvent dissolves the salt well to help the movement of the lithium ions, and the additive is added to improve specific performance according to required characteristics of the lithium secondary battery.

The additive may perform various roles depending on a type thereof, and a representative role among them is to form a solid electrolyte interface (SEI) on a surface of an electrode. The lithium secondary battery has a problem in that a positive electrode active material is structurally collapsed as charge and discharge proceed, and metal ions dissolved from a surface of the collapsed positive electrode are electrodeposited on the negative electrode to degrade performance of the positive electrode and the negative electrode. In this case, if the additive is included in the electrolyte solution, the additive may be decomposed during initial charge and discharge to form a film called a solid electrolyte interface (SEI) on the surface of the electrode, and the formed SEI may play a role in improving battery characteristics, storage characteristics, or load characteristics by preventing performance degradation when charge and discharge cycles are repeated while not interfering with the movement of the lithium ions.

Specifically, the SEI formed during the initial charge and discharge prevents a reaction between the lithium ions and a carbon-based negative electrode or other materials during subsequent repeated charge and discharge, and acts as an ion tunnel that selectively passes only the lithium ions between the electrolyte solution and the negative electrode. The SEI prevents collapse of a carbon-based negative electrode structure by blocking movement of organic solvents of the electrolyte solution having a large molecular weight to the carbon-based negative electrode due to the ion tunnel effect. That is, since occurrence of a side reaction between the lithium ions and the carbon-based negative electrode or other materials is suppressed by the formed SEI, an amount of the lithium ions may be reversibly maintained during subsequent charge and discharge.

In other words, since a carbon material of the negative electrode reacts with the electrolyte solution during initial charge to form a passivation layer on the surface of the negative electrode, it allows that no further electrolyte solution decomposition occurs and stable charge and discharge may be maintained, wherein, in this case, an amount of charge consumed to form the passivation layer on the surface of the negative electrode, as irreversible capacity, has a characteristic that does not react reversibly during discharge, and, for this reason, a lithium ion battery may maintain a stable life cycle without exhibiting any more irreversible reaction after the initial charge reaction.

However, in a case in which the lithium ion battery is stored at a high temperature in a fully charged state (e.g.: stored at 60° C. after being charged to 100% at 4.15 V or more), there is a problem in that the SEI gradually collapses over time. The collapse of the SEI exposes the surface of the negative electrode, and the exposed surface of the negative electrode is decomposed while reacting with a carbonate-based solvent in the electrolyte solution to cause a continuous side reaction. Furthermore, the side reaction continuously generates gases. The gases generated by the side reaction increase an internal pressure of the battery regardless of their types, and act as a resistance element to lithium movement to be a cause of expansion of a thickness of the battery and degradation of battery performance.

Thus, in order to provide a lithium secondary battery capable of achieving excellent and stable performance, there is a need for an additive capable of forming an SEI, which is stable and not easily decomposed, and preventing the formed SEI from adversely affecting electrode performance.

Prior Art Document (Patent Document 1) JP 2019-179638 A
(Patent Document 2) JP 2018-156761 A

DISCLOSURE OF THE INVENTION

Technical Problem

An aspect of the present invention provides a compound having a cyclic sulfur oxide structure, which may achieve excellent cycle characteristics of a lithium secondary battery and an improved effect in terms of high-temperature stability and gas generation, and a non-aqueous electrolyte solution additive including the same.

Another aspect of the present invention provides a non-aqueous electrolyte solution including the non-aqueous electrolyte solution additive and a lithium secondary battery including the non-aqueous electrolyte solution.

Technical Solution

In order to solve the above-described tasks, the present invention provides a novel compound, a non-aqueous electrolyte solution additive and a non-aqueous electrolyte solution which include the above compound, and a lithium secondary battery including the non-aqueous electrolyte solution.

(1) The present invention provides a compound represented by Formula 1:

[Formula 1]

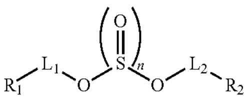

In Formula 1, n is 1 or 2, $L_1$ and $L_2$ are each independently a direct bond or an unsubstituted or substituted C1 to C6 alkylene group, and $R_1$ and $R_2$ are each independently a substituent represented by Formula 2,

[Formula 2]

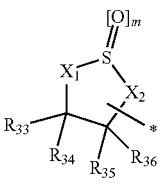

In Formula 2, m is 1 or 2, $X_1$ and $X_2$ are each independently —O— or —C($R_{31}$)($R_{32}$)—, wherein at least one of $X_1$ or $X_2$ is —O—, and $R_{31}$ to $R_{36}$ are each independently hydrogen, a C1 to C6 alkyl group, —C(═O)—$R_4$, or —$R_5$—O—C(═O)—$R_6$, wherein $R_4$ and $R_6$ are each independently an unsubstituted or substituted C1 to C6 alkyl group, a C2 to C20 alkenyl group, a C2 to C20 alkynyl group, or an unsubstituted or substituted C6 to C20 aryl group, $R_5$ is an unsubstituted or substituted C1 to C6 alkylene group, substituents of $L_1$, $L_2$, $R_4$, $R_5$, and $R_6$ are each independently at least one selected from the group consisting of deuterium, —F, —Cl, —Br, —I, —ON, —$NO_2$, and —$SO_3$, and

* is a position bonded to $L_1$ or $L_2$, wherein, in a case in which both $L_1$ and $L_2$ are direct bonds, $R_1$ and $R_2$ are not simultaneously CS-7, and in a case in which n is 2 while both $L_1$ and $L_2$ are methylene groups, $R_1$ and $R_2$ are not simultaneously CS-2.

CS-2

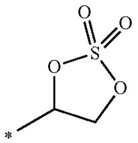

CS-7

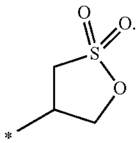

(2) The present invention provides the compound of (1) above, wherein $R_1$ and $R_2$ are each independently selected from the group consisting of CS-1 to CS-15:

CS-1

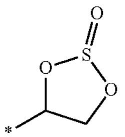

CS-2

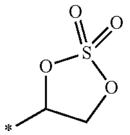

CS-3

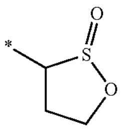

CS-4

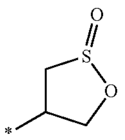

CS-5

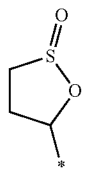

CS-6

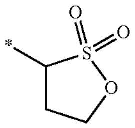

CS-7

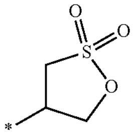

-continued

CS-8

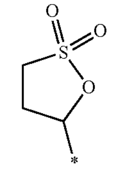

CS-9

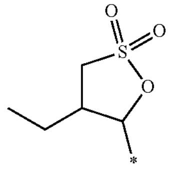

CS-10

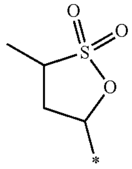

CS-11

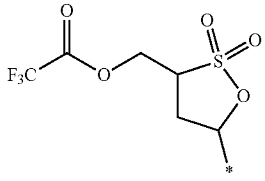

CS-12

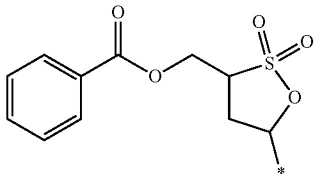

CS-13

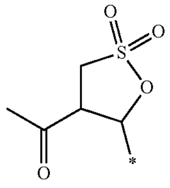

CS-14

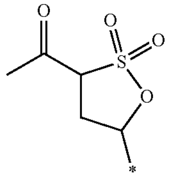

CS-15

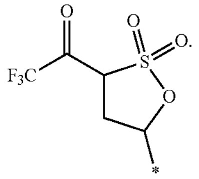

(3) The present invention provides the compound of (1) or (2) above, wherein $L_1$ and $L_2$ are methylene groups.

(4) The present invention provides the compound of any one of (1) to (3) above, wherein $R_1$ and $R_2$ are each independently any one selected from the group consisting of CS-1, CS-2, CS-5, CS-8, CS-10, and CS-11.

(5) The present invention provides the compound of any one of (1) to (4) above, wherein the compound is any one selected from the group consisting of compounds A to R:

A

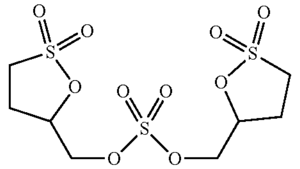

B

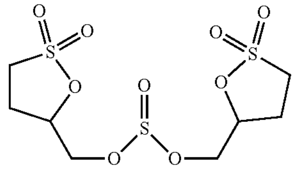

C

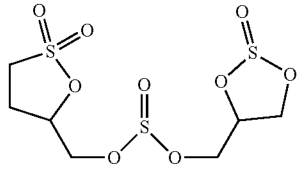

D

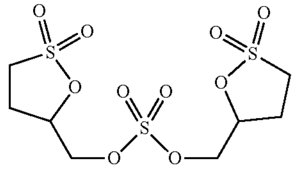

E

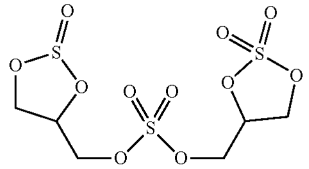

F

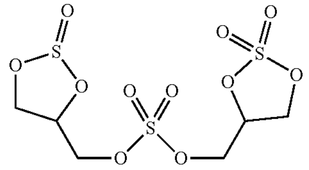

G

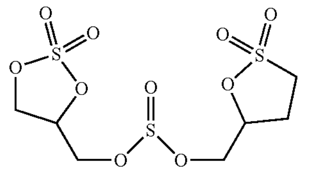

H

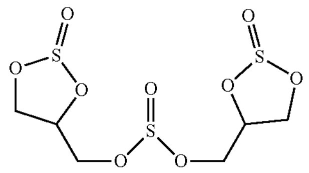

-continued

I

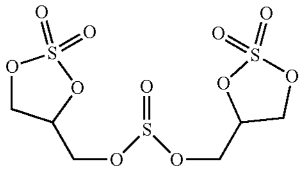

J

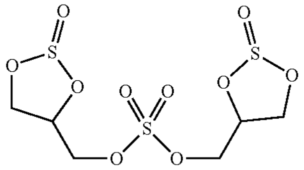

K

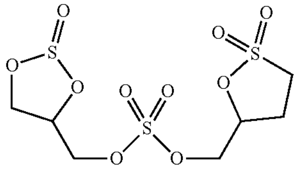

L

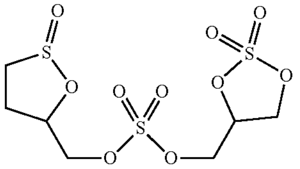

M

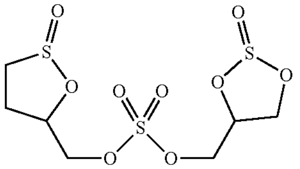

N

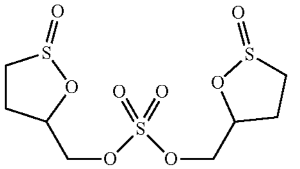

O

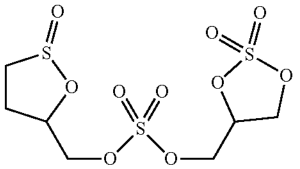

P

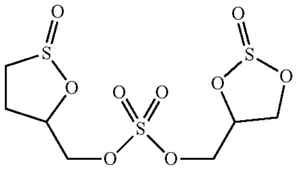

Q

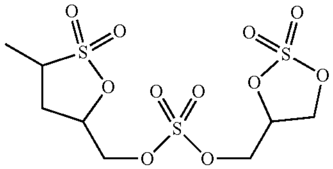

-continued

R

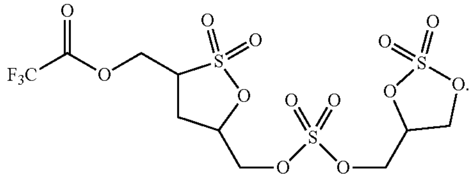

(6) The present invention provides a non-aqueous electrolyte solution additive including the compound of any one of (1) to (5).

(7) The present invention provides a non-aqueous electrolyte solution including a lithium salt, a non-aqueous solvent, and the non-aqueous electrolyte solution additive of (6).

(8) The present invention provides the non-aqueous electrolyte solution of (7) above, wherein the non-aqueous electrolyte solution additive is included in an amount of 0.01 wt % to 10 wt % based on a total weight of the non-aqueous electrolyte solution.

(9) The present invention provides the non-aqueous electrolyte solution of (7) or (8) above, wherein the lithium salt is at least one selected from the group consisting of LiCl, LiBr, LiI, $LiBF_4$, $LiClO_4$, $LiB_{10}Cl_{10}$, $LiAlCl_4$, $LiAlO_4$, $LiPF_6$, $LiCF_3SO_3$, $LiCH_3CO_2$, $LiCF_3CO_2$, $LiAsF_6$, $LiSbF_6$, $LiCH_3SO_3$, LiFSI (lithium bis(fluorosulfonyl)imide, $LiN(SO_2F)_2$), LiBETI (lithium bisperfluoroethanesulfonimide, $LiN(SO_2CF_2CF_3)_2$), and LiTFSI (lithium (bis)trifluoromethanesulfonimide, $LiN(SO_2CF_3)_2$).

(10) The present invention provides the non-aqueous electrolyte solution of any one of (7) to (9) above, wherein the non-aqueous solvent is at least one selected from the group consisting of a cyclic carbonate-based organic solvent, a linear carbonate-based organic solvent, a cyclic ester-based organic solvent, and a linear ester-based organic solvent.

(11) The present invention provides a lithium secondary battery including a positive electrode, a negative electrode, a separator, and the non-aqueous electrolyte solution of any one of (7) to (10).

Advantageous Effects

A compound of the present invention may be obtained in acceptable synthetic yield, and storage stability of the compound is also satisfactory. Also, the compound of the present invention may improve lifetime of a battery by forming a stable solid electrolyte interface (SEI) with low resistance when the compound is used as an additive of a non-aqueous electrolyte solution and may also simultaneously improve stability at high temperatures by reducing an amount of gas generated.

MODE FOR CARRYING OUT THE INVENTION

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

Compound Represented by Formula 1

The present invention provides a compound represented by Formula 1 below:

[Formula 1]

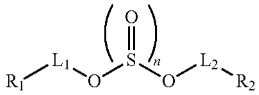

In Formula 1, n is 1 or 2, $L_1$ and $L_2$ are each independently a direct bond or an unsubstituted or substituted C1 to C6 alkylene group, and $R_1$ and $R_2$ are each independently a substituent represented by Formula 2 below,

[Formula 2]

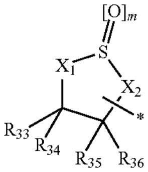

In Formula 2, m is 1 or 2, $X_1$ and $X_2$ are each independently —O— or —C($R_{31}$)($R_{32}$)—, wherein at least one of $X_1$ or $X_2$ is —O—, and $R_{31}$ to $R_{36}$ are each independently hydrogen, a C1 to C6 alkyl group, —C(=O)—$R_4$, or —$R_5$—O—C(=O)—$R_6$, wherein $R_4$ and $R_6$ are each independently an unsubstituted or substituted C1 to C6 alkyl group, a C2 to C20 alkenyl group, a C2 to C20 alkynyl group, or an unsubstituted or substituted C6 to C20 aryl group, $R_5$ is an unsubstituted or substituted C1 to C6 alkylene group, substituents of $L_1$, $L_2$, $R_4$, $R_5$, and $R_6$ are each independently at least one selected from the group consisting of deuterium, —F, —Cl, —Br, —I, —CN, —$NO_2$, and —$SO_3$, and

* is a position bonded to $L_1$ or $L_2$, wherein, in a case in which both $L_1$ and $L_2$ are direct bonds, $R_1$ and $R_2$ are not simultaneously CS-7 below, and in a case in which n is 2 while both $L_1$ and $L_2$ are methylene groups, $R_1$ and $R_2$ are not simultaneously CS-2 below.

CS-2

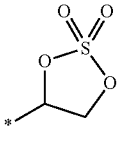

-continued

CS-7

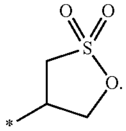

The compound represented by Formula 1, which is provided by the present invention, is characterized in that it includes a sulfur oxide structure in a center and simultaneously has a cyclic sulfur oxide structure at both ends, wherein the compound represented by Formula 1 may induce stable formation of anions in a non-aqueous electrolyte solution by employing this chemical structure when it is used as an additive of the non-aqueous electrolyte solution, and, furthermore, may form a stable solid electrolyte interface (SEI). Specifically, the compounds represented by Formula 1 may efficiently induce film formation by including two or more $SO_x$ (2≤x≤4) functional groups in one molecule. Specifically, the compound represented by Formula 1 is reduced faster than a non-aqueous solvent in the electrolyte solution during charge and discharge to be able to form a robust film containing $LiSO_x$ (2≤x≤4) before a side reaction occurs, and, accordingly, an increase in interfacial resistance may not only be minimized, but exposure of an surface of an electrode may also be prevented to suppress the side reaction between the electrode and the electrolyte solution. Subsequently, dissolution of transition metals from a positive electrode due to collapse of the film may be effectively controlled, and a lithium secondary battery, in which a battery swelling phenomenon does not occur while having excellent high-temperature storage characteristics and high-temperature cycle characteristics, may be achieved.

The compound represented by Formula 1 has a reduction potential of 0.5 eV or more, wherein, since the reduction potential is higher than that of the non-aqueous solvent, the compound may first be decomposed under cell operation conditions to form a robust film, and the reduction potential may be measured by the following method using a Gaussian 09 program package (Gaussian 09 Revision C.01, Gaussian Inc., Wallingford, CT, 2009) to which a density functional theory (DFT) calculation method is applied.

1) Calculate stable structural energy (Eneut) of the compound in a pre-reduced state, and stable structural energy (Ered) of the compound in a reduced state.
2) Eneut-Ered-1.45 eV is defined as a reduction stability value.
3) In this case, structural stabilization calculation is performed in a state in which a polarizable continuum model (PCM) method is used.

More specifically, $R_1$ and $R_2$ in the compound represented by Formula 1 of the present invention may each independently be selected from the group consisting of CS-1 to CS-15 below:

CS-1

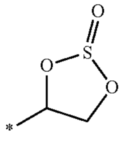

-continued

CS-2

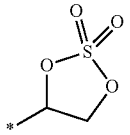

CS-3

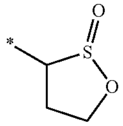

CS-4

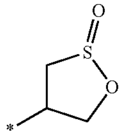

CS-5

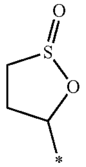

CS-6

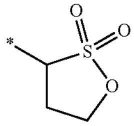

CS-7

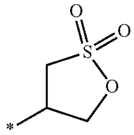

CS-8

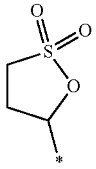

CS-9

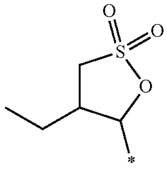

CS-10

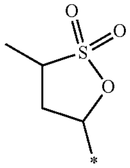

CS-11

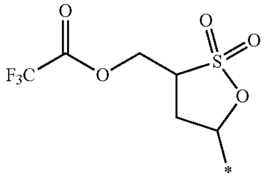

-continued

CS-12

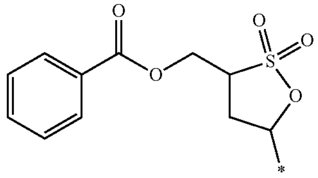

CS-13

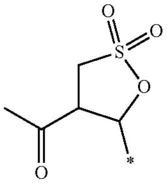

CS-14

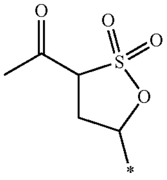

CS-15

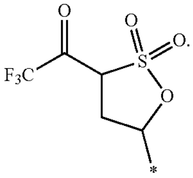

The substituent structures CS-1 to CS-15 listed above are preferred examples of $R_1$ and $R_2$ of Formula 1, and, when the substituents of CS-1 to CS-15 are used as $R_1$ and $R_2$ of Formula 1, a function as a non-aqueous electrolyte solution additive may be smoothly performed while overall structural stability of the compound is excellent. Particularly, it may be desirable in terms of structural stability and ease of synthesis that $R_1$ and $R_2$ are each independently any one selected from the group consisting of CS-1, CS-2, CS-5, CS-8, CS-10, and CS-11.

In the compound represented by Formula 1 of the present invention, in a case in which $R_1$ and $R_2$ are CS-7 while both $L_1$ and $L_2$ are direct bonds, or, in a case in which n is 2 while both $L_1$ and $L_2$ are methylene groups and $R_1$ and $R_2$ are CS-2 at the same time, since the structural stability of the compound itself is low, the compound may be easily decomposed, and thus the synthesis of the compound itself may be difficult. Particularly, compounds satisfying the above conditions have disadvantages in that $R_1$ and $R_2$ structures having a ring form are easily decomposed during a synthesis process, the compounds may be easily decomposed during storage even if the compounds are finally synthesized, and synthetic yield is also significantly low. Thus, in the present invention, compounds, in which $R_1$ and $R_2$ are CS-7 while both $L_1$ and $L_2$ are direct bonds and in which $R_1$ and $R_2$ are CS-2 at the same time while n is 2, are excluded.

In the compound represented by Formula 1, $L_1$ and $L_2$ may each independently be a direct bond, a methylene group, or an ethylene group, and may be particularly a methylene group. When $L_1$ and $L_2$ are methylene groups, the synthesis of the compound may be easy, and the decomposition of the compound after the synthesis may be suppressed.

More specifically, it may be particularly desirable that the compound is any one selected from the group consisting of compounds A to R below:
A
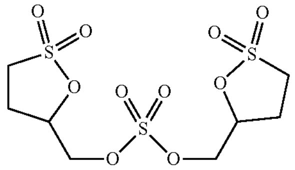
B
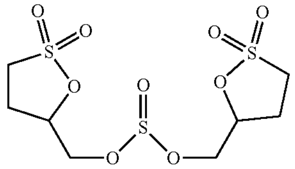
C
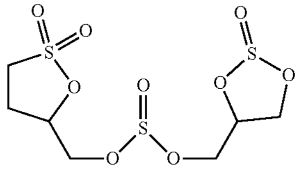
D
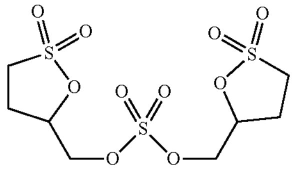
E
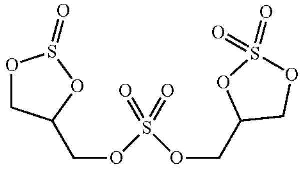
F
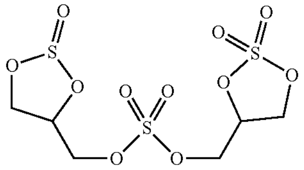
G
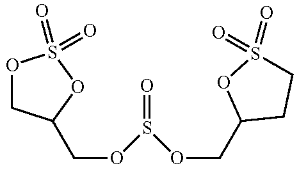
H
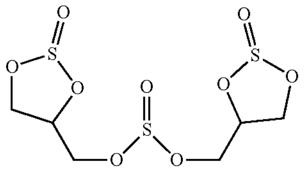
-continued
I
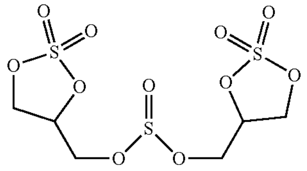
J
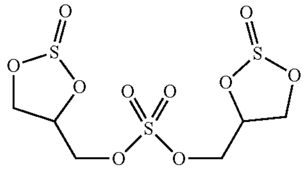
K
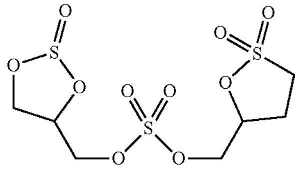
L
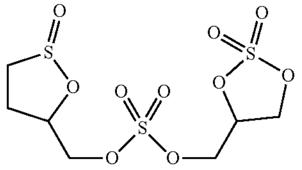
M
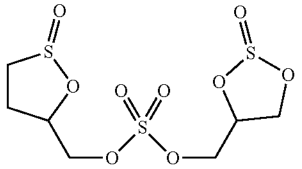
N
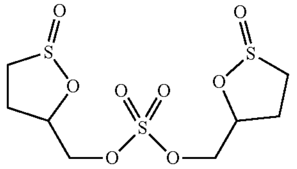
O
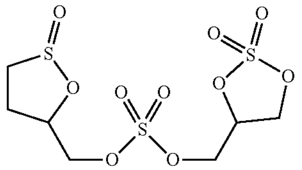
P
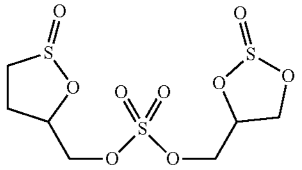
Q
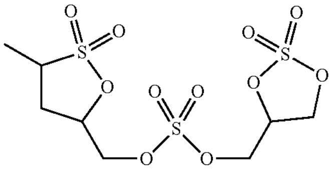

-continued

R

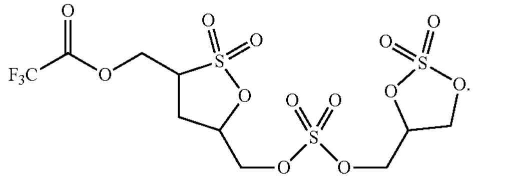

In a case in which the compound represented by Formula 1 has the structure that is described as desirable above, there is an advantage in that a stable SEI with low resistance may be formed even with an amount smaller than that of a conventionally used additive.

Non-Aqueous Electrolyte Solution Additive

The present invention provides a non-aqueous electrolyte solution additive including the compound represented by Formula 1 described above. As described above, when the compound represented by Formula 1 is used as the additive of the non-aqueous electrolyte solution, a stable SEI may be formed and excellent high-temperature storage characteristics and high-temperature cycle characteristics may be provided by preventing the exposure of the surface of the electrode.

The non-aqueous electrolyte solution additive provided by the present invention may include other compounds, which are known to be usable as a non-aqueous electrolyte solution additive, in addition to the compound represented by Formula 1. Specific types of the other compounds included together are not particularly limited, and any compound may be used as long as it may be used as a non-aqueous electrolyte solution additive without impairing an effect of the compound represented by Formula 1. For example, the compounds, which may be used together, may be vinylene carbonate (VC), fluoroethylene carbonate (FEC), 1,3-propane sultone (PS), and ethylene sulfate (Esa).

Non-Aqueous Electrolyte Solution

The present invention provides a non-aqueous electrolyte solution including the above-described non-aqueous electrolyte solution additive, a lithium salt, and a non-aqueous solvent. The non-aqueous electrolyte solution additive is the same as described above, and the non-aqueous electrolyte solution additive may be included in an amount of 0.01 wt % to 10 wt %, preferably 0.1 wt % to 8 wt %, and particularly preferably 0.5 wt % to 6 wt % based on a total weight of the non-aqueous electrolyte solution. In a case in which the additive is included in an amount within the above-described range, an improvement in discharge stability and charge and discharge efficiency may be maximized while suppressing performance degradation due to the side reaction as much as possible.

1) Lithium Salt

The non-aqueous electrolyte solution of the present invention includes a lithium salt. The lithium salt is a component for providing lithium ions in the electrolyte solution, wherein any lithium salt typically used in a non-aqueous electrolyte solution of a lithium secondary battery may be used without particular limitation.

For example, one including $Li^+$ as a cation and including at least one selected from the group consisting of $F^-$, $Cl^-$, $Br^-$, $I^-$, $NO_3^-$, $N(CN)_2^-$, $BF_4^-$, $ClO_4$, $B_{10}Cl_{10}^-$, $AlCl_4^-$, $AlO_4^-$, $PF_6^-$, $CF_3SO_3^-$, $CH_3CO_2^-$, $CF_3CO_2^-$, $AsF_6^-$, $SbF_6^-$, $CH_3SO_3^-$, $(CF_3CF_2SO_2)_2N^-$, $(CF_3SO_2)_2N^-$, $(FSO_2)_2N^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $C_4F_9SO_3^-$, $CF_3CF_2SO_3^-$, $CF_3CF_2(CF_3)_2CO^-$, $(CF_3SO_2)_2CH^-$, $CF_3(CF_2)_7SO^{3-}$, and $SCN^-$ as a counter ion thereof may be used as the lithium salt.

Specifically, the lithium salt may include at least one selected from the group consisting of LiCl, LiBr, LiI, $LiBF_4$, $LiClO_4$, $LiB_{10}Cl_{10}$, $LiAlCl_4$, $LiAlO_4$, $LiPF_6$, $LiCF_3SO_3$, $LiCH_3CO_2$, $LiCF_3CO_2$, $LiAsF_6$, $LiSbF_6$, $LiCH_3SO_3$, lithium bis(fluorosulfonyl)imide (LiFSI, $LiN(SO_2F)_2$), lithium bisperfluoroethanesulfonimide (LiBETI, $LiN(SO_2CF_2CF_3)_2$), and lithium (bis)trifluoromethanesulfonimide (LiTFSI, $LiN(SO_2CF_3)_2$).

A concentration of the lithium salt in the non-aqueous electrolyte solution may be appropriately adjusted according to a purpose within a normally acceptable range, and, for example, may be in a range of 0.5 M to 5.0 M, specifically, M to 4.0 M or 1.0 M to 3.0 M. In a case in which the concentration of the lithium salt is excessively low, mobility of lithium ions may be reduced to degrade output or cycle characteristics of the lithium secondary battery, and, in a case in which the concentration of the lithium salt is excessively high, viscosity of the non-aqueous electrolyte solution may be increased to reduce impregnability of the electrolyte solution.

2) Non-Aqueous Solvent

The non-aqueous electrolyte solution of the present invention includes a non-aqueous solvent for dissolving the lithium salt and the additive. Specifically, at least one selected from the group consisting of a cyclic carbonate-based organic solvent, a linear carbonate-based organic solvent, a cyclic ester-based organic solvent, and a linear ester-based organic solvent may be used as the non-aqueous solvent, and, particularly, a cyclic carbonate-based organic solvent, a linear carbonate-based organic solvent, or a mixed organic solvent thereof may be used.

The cyclic carbonate-based organic solvent is an organic solvent which may well dissociate the lithium salt in an electrolyte due to high permittivity as a highly viscous organic solvent, wherein specific examples thereof may be at least one organic solvent selected from the group consisting of ethylene carbonate (EC), propylene carbonate (PC), 1,2-butylene carbonate, 2,3-butylene carbonate, 1,2-pentylene carbonate, 2,3-pentylene carbonate, and vinylene carbonate, and, among them, the cyclic carbonate-based organic solvent may include ethylene carbonate.

The linear carbonate-based organic solvent is an organic solvent having low viscosity and low permittivity, wherein typical examples thereof may be at least one organic solvent selected from the group consisting of dimethyl carbonate (DMC), diethyl carbonate (DEC), dipropyl carbonate, ethyl methyl carbonate (EMC), methylpropyl carbonate, and ethylpropyl carbonate, and the linear carbonate-based organic solvent may specifically include ethyl methyl carbonate (EMC).

In addition to the cyclic carbonate-based organic solvent and/or the linear carbonate-based organic solvent, at least one ester-based organic solvent selected from the group consisting of a linear ester-based organic solvent and a cyclic ester-based organic solvent may be additionally included to further increase ionic conductivity.

Specific examples of the linear ester-based organic solvent may be at least one organic solvent selected from the group consisting of methyl acetate, ethyl acetate, propyl acetate, methyl propionate, ethyl propionate, propyl propionate, and butyl propionate.

Also, the cyclic ester-based organic solvent may include at least one organic solvent selected from the group consisting of γ-butyrolactone, γ-valerolactone, γ-caprolactone, σ-valerolactone, and ε-caprolactone.

In addition to the above-described organic solvent, any organic solvent typically used in a non-aqueous electrolyte solution for a lithium secondary battery may be added and used without limitation, if necessary. For example, at least one organic solvent selected from an ether-based organic solvent, an amide-based organic solvent, or a nitrile-based organic solvent may be further included.

3) Additive for Forming SEI

The non-aqueous electrolyte solution of the present invention may further include additives for forming an SEI in the non-aqueous electrolyte solution, if necessary, in order to prevent the occurrence of the collapse of the negative electrode due to the decomposition of the non-aqueous electrolyte solution in a high output environment or to further improve low-temperature high rate discharge characteristics, high-temperature stability, overcharge prevention, and an effect of suppressing battery swelling at high temperature.

Typical examples of the additive for forming an SEI may include at least one additive for forming an SEI which is selected from the group consisting of a cyclic carbonate-based compound, a halogen-substituted carbonate-based compound, a sultone-based compound, a sulfate-based compound, a phosphate-based compound, a borate-based compound, a nitrile-based compound other than decanenitrile and 1,4-dicyano-2-butene, a benzene-based compound, an amine-based compound, a silane-based compound, and a lithium salt-based compound.

The cyclic carbonate-based compound may include vinylene carbonate (VC) or vinyl ethylene carbonate, and may be included in an amount of 3 wt % or less based on the total weight of the non-aqueous electrolyte solution. In a case in which the amount of the cyclic carbonate-based compound in the electrolyte is greater than 3 wt %, cell swelling inhibition performance may be degraded.

The halogen-substituted carbonate-based compound may include fluoroethylene carbonate (FEC), and may be included in an amount of 5 wt % or less based on a total weight of the electrolyte. In a case in which the amount of the halogen-substituted carbonate-based compound in the electrolyte is greater than 5 wt %, the cell swelling inhibition performance may be degraded.

The sultone-based compound may include at least one compound selected from the group consisting of 1,3-propane sultone (PS), 1,4-butane sultone, ethane sultone, 1,3-propene sultone (PRS), 1,4-butene sultone, and 1-methyl-1, 3-propene sultone.

The sultone-based compound may be included in an amount of 0.3 wt % to 5 wt %, for example, 1 wt % to 5 wt % based on the total weight of the non-aqueous electrolyte solution. In a case in which the amount of the sultone-based compound in the electrolyte is greater than 5 wt %, an excessively thick film may be formed on the surface of the electrode to cause an increase in resistance and degradation of output, and an increase in resistance due to the excessive amount of the additive in the electrolyte may degrade output characteristics.

The sulfate-based compound may include ethylene sulfate (Esa), trimethylene sulfate (TMS), or methyl trimethylene sulfate (MTMS), and may be included in an amount of 5 wt % or less based on the total weight of the electrolyte.

The phosphate-based compound may include at least one compound selected from the group consisting of lithium difluoro bis(oxalato)phosphate, lithium difluorophosphate, tetramethyl trimethyl silyl phosphate, trimethyl silyl phosphite, tris(2,2,2-trifluoroethyl)phosphate, and tris(trifluoroethyl)phosphite, and may be included in an amount of 5 wt % or less based on the total weight of the electrolyte.

The borate-based compound may include tetraphenylborate and lithium oxalyldifluoroborate, and may be included in an amount of 5 wt % or less based on the total weight of the electrolyte.

The nitrile-based compound is a nitrile-based compound other than decanenitrile (DN) and 1,4-dicyano-2-butene (DCB), wherein typical examples of the nitrile-based compound may be at least one compound selected from the group consisting of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, 4-fluorophenylacetonitrile, and 1,3,6-hexanetricarbonitrile.

The nitrile-based compound may be included in an amount of 5 wt % to 8 wt %, for example, 6 wt % to 8 wt % based on the total weight of the non-aqueous electrolyte solution. In a case in which the amount of the nitrile-based compound in the electrolyte is greater than 8 wt %, since the resistance is increased due to an increase in the film formed on the surface of the electrode, battery performance may be degraded.

The benzene-based compound may include fluorobenzene, the amine-based compound may include triethanolamine or ethylenediamine, and the silane-based compound may include tetravinylsilane.

The lithium salt-based compound is a compound different from the lithium salt included in the non-aqueous electrolyte solution, wherein the lithium salt-based compound may include at least one compound selected from the group consisting of $LiPO_2F_2$, LiODFB, LiBOB (lithium bis(oxalate)borate ($LiB(C_2O_4)_2$), and $LiBF_4$, and may be included in an amount of 5 wt % or less based on the total weight of the electrolyte.

In a case in which, among these additives for forming an SEI, vinylene carbonate, vinyl ethylene carbonate, or succinonitrile is additionally included, a more robust SEI may be formed on the surface of the negative electrode during an initial activation process of the secondary battery.

In a case in which the $LiBF_4$ is included, high-temperature stability of the secondary battery may be improved by suppressing generation of a gas which may be generated due to the decomposition of the electrolyte solution during high-temperature storage.

Two or more additives for forming an SEI may be mixed and used, and the additive for forming an SEI may be included in an amount of 0.1 wt % to 50 wt %, particularly 0.01 wt % to 10 wt %, and preferably 0.05 wt % to 5 wt % based on the total weight of the non-aqueous electrolyte solution. If the amount of the additive for forming an SEI is less than 0.01 wt %, an effect of improving low-temperature output, high-temperature storage characteristics, and high-temperature life characteristics of the battery is insignificant, and, if the amount of the additive for forming an SEI is greater than 50 wt %, the side reaction in the electrolyte solution may excessively occur during charge and discharge of the battery. Particularly, when the excessive amount of the additives for forming an SEI is added, the additives may not be sufficiently decomposed at high temperature so that they may be present in the form of an unreacted material or precipitates in the electrolyte solution at room temperature. Accordingly, a side reaction that degrades life or resistance characteristics of the secondary battery may occur.

Lithium Secondary Battery

In another embodiment of the present invention, there is provided a lithium secondary battery including the non-aqueous electrolyte solution of the present invention.

After an electrode assembly, in which a positive electrode, a negative electrode, and a separator between the positive electrode are sequentially stacked, is formed and accommodated in a battery case, the lithium secondary battery provided by the present invention may be prepared by injecting the non-aqueous electrolyte solution of the present invention.

The positive electrode, the negative electrode, and the separator, which are included in the lithium secondary battery of the present invention, may be prepared according to a conventional method known in the art and used, and are specifically the same as those described later.

1) Positive Electrode

The positive electrode may be prepared by coating a positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium transition metal oxide including lithium and at least one metal such as cobalt, manganese, nickel, or aluminum.

More specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$). $LiMn_{2-Z}Ni_ZO_4$ (where $0<Z<2$)), lithium-nickel-cobalt-based oxide (e.g., $LiNi_{1-Y1}Co_{Y1}O_2$ (where $0<Y1<1$)), lithium-manganese-cobalt-based oxide (e.g., $LiCo_{1-Y2}Mn_{Y2}O_2$ (where $0<Y2<1$), $LiMn_{2-Z1}Co_{z1}O_3$ (where $0<Z1<2$)), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), or lithium-nickel-cobalt-transition metal (M) oxide (e.g., $Li(Ni_{p2}Co_{q2}Mn_{r3}M_{S2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), and any one thereof or a compound of two or more thereof may be included. Among these materials, in terms of the improvement of cycle characteristics and stability of the battery, the lithium composite metal oxide may include $LiCoO_2$, $LiMnO_2$, $LiNiO_2$, lithium nickel manganese cobalt oxide (e.g., $Li(Ni_{0.6}Mn_{0.2}Co_{0.2})O_2$, $Li(Ni_{0.5}Mn_{0.3}Co_{0.2})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.), and, in consideration of a significant improvement due to the control of type and content ratio of elements constituting the lithium composite metal oxide, the lithium composite metal oxide may be $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$, and any one thereof or a mixture of two or more thereof may be used.

The positive electrode active material may be included in an amount of 80 wt % to 99 wt %, for example, 90 wt % to 99 wt % based on a total weight of solid content in the positive electrode slurry. In this case, when the amount of the positive electrode active material is less than 80 wt %, since energy density is reduced, capacity may be reduced.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene ter monomer, a styrene-butadiene rubber, a fluoro rubber, or various copolymers.

Also, the conductive agent is a material providing conductivity without causing adverse chemical changes in the battery, wherein it may be added in an amount of 1 wt % to 20 wt % based on the total weight of the solid content in the positive electrode slurry.

As a typical example of the conductive agent, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

Furthermore, the solvent may include an organic solvent, such as N-methyl-2-pyrrolidone (NMP), and may be used in an amount such that desirable viscosity is obtained when the positive electrode active material as well as optionally the binder and the conductive agent are included. For example, the solvent may be included in an amount such that a concentration of the solid content in the positive electrode slurry including the positive electrode active material as well as optionally the binder and the conductive agent is in a range of 10 wt % to 60 wt %, for example, 20 wt % to 50 wt %.

2) Negative Electrode

The negative electrode may be prepared by coating a negative electrode collector with a negative electrode slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metal or an alloy of lithium and the metal, a metal composite oxide, a material which may be doped and undoped with lithium, and a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metal or the alloy of lithium and the metal, a metal selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn), or an alloy of lithium and the metal may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \leq x \leq 1$), $Li_xWO_2$ ($1 \leq x \leq 1$), and $Sn_xMe_{1-x}Me'_yO_z$ (Me: manganese (Mn), Fe, Pb, or Ge; Me': Al, boron (B), phosphorus (P), Si, Groups I, II and III elements of the periodic table, or halogen; $0<x\leq 1$; $1\leq y\leq 3$; $1\leq z\leq 8$) may be used as the metal composite oxide.

The material, which may be doped and undoped with lithium, may include Si, $SiO_x$ ($0<x\leq 2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), rutherfordium (Rf), V, niobium (Nb), Ta, dubnium (Db), Cr, Mo, tungsten (W), seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), polonium (Po), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride, polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene monomer, a styrene-butadiene rubber, a fluoro rubber, or various copolymers thereof.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; conductive powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as optionally the binder and the conductive agent are included. For example, the solvent may be included in an amount such that a concentration of the solid content in the negative electrode slurry including the negative electrode active material as well as optionally the binder and the conductive agent is in a range of 50 wt % to 75 wt %, for example, 50 wt % to 65 wt %.

3) Separator

A typical porous polymer film generally used, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator included in the lithium secondary battery of the present invention, and a typical porous nonwoven fabric, for example, a nonwoven fabric formed of high melting point glass fibers or polyethylene terephthalate fibers may be used, but the present invention is not limited thereto.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

SYNTHESIS EXAMPLES

Each compound was synthesized through the following method.

1) Synthesis of Compound B 5 g of 3-butene-1,2-diol (but-3-ene-1,2-diol), 11.5 g of $Na_2S_2O_5$, and 10 g of water were put in a flask, and stirred at 65° C. for 9 hours while maintaining a pH of 7.3. The reaction solution was concentrated by vacuum distillation, and 50 mL of methanol was added thereto to obtain a precipitate. The precipitate was vacuum-filtered and then dried in a vacuum oven to obtain 10 g of sodium 3,4-dihydroxybutane sulfonate.

Then, 10 g of the dried sodium 3,4-dihydroxybutane sulfonate, 0.2 g of DMF, and 70 g of THF were put in a flask, and 10 g of thionyl chloride was slowly dispensed at 0° C. After the dispensing was completed, the reactant was heated at 60° C. for 2 hours, the heated reactant was then cooled to room temperature, and HCl and MeOH were added thereto. Thereafter, the reactant was passed through a silica column and then concentrated under reduced pressure to obtain 5 g of 3-hydroxymethyl-1,3-propane sultone.

Then, 30 g of ethyl acetate and 3 g of pyridine were put in a flask, and 2.2 g of thionyl chloride was slowly added at 0° C. After stirring at room temperature for 30 minutes, 5 g of the previously obtained 3-hydroxymethyl-1,3-propane sultone was dissolved in 20 g of ethyl acetate and slowly added. After reacting for 2 hours, the product was extracted into an organic layer using water and methylene chloride, and the extracted organic layer was concentrated to obtain bis((2,2-dioxido-1,2-oxathiolan-5-yl)methyl) sulfite (the following Compound B).

[Compound B]

B

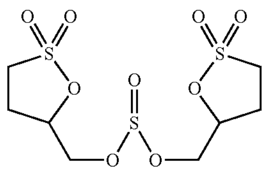

Whether or not the compound was synthesized was confirmed by $^1$H-NMR.

$^1$H-NMR (500 MHz, Bruker, ACN-d3)=4.9 (2H), 4.28 (2H), 4.15 (2H), 3.35 (4H), 2.6 (2H), 2.4 (2H)

2) Synthesis of Compound A 5 g of the Compound B obtained by vacuum drying in Synthesis Example 1), 40 g of acetonitrile, and 20 g of water were put in a flask. Thereafter, 0.03 g of $RuCl_3$ and 4 g of $NaIO_4$, which were dissolved in 30 g of water at 0° C., were slowly added dropwise and stirred. After 30 minutes of reaction, 100 g of t-butyl ether was added and stirred, an organic layer was then separated and extracted with water and ethyl acetate, and, after the extraction, the organic layer was concentrated under reduced pressure to obtain bis((2,2-dioxido-1,2-oxathiolan-5-yl)methyl) sulfate (the following Compound A).

[Compound A]

A

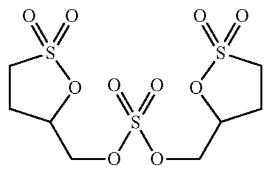

Whether or not the compound was synthesized was confirmed by $^1$H-NMR.

$^1$H-NMR (500 MHz, Bruker, ACN-d3)=5.1 (2H), 4.7 (2H), 4.6 (2H), 3.5 (4H), 2.9 (2H), 2.4 (2H)

3) Synthesis of Compound C 5 g of moisture-controlled glycerol and 90 g of dimethyl carbonate (DMC) were put in a flask, and 13 g of thionyl chloride was then slowly added dropwise at 0° C. After a reaction was completed, vacuum distillation was performed to remove both reaction solvent and generated HCl, and 90 g of dimethyl carbonate was additionally added. Thereafter, 8.3 g of the 3-hydroxymethyl-1,3-propane sultone prepared in Synthesis Example 1) was dissolved in 10 g of dimethyl carbonate, and then slowly added dropwise at 0° C. After 3 hours of reaction, extraction was performed using water and ethyl acetate, and an organic layer was dried under reduced pressure to obtain ((2,2-dioxido-1,2-oxathiolan-5-yl)methyl) (2-oxido-1,3,2-dioxathiolan-4-yl)methyl) sulfite (the following Compound C).

[Compound C]

C

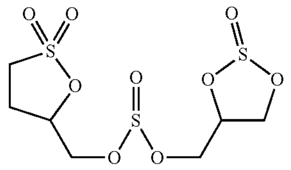

The Compound C is characterized in that it exists in a form in which stereoisomers are mixed in a molar ratio of 6:4 due to a cyclic sulfite structure, and whether or not the compound was synthesized was confirmed by $^1$H-NMR.

$^1$H-NMR (500 MHz, Bruker, $CDCl_3$)=5.1 (0.6H), 4.9 (1H), 4.8 (1H), 4.6 (0.6H), 4.4~4.0 (4.8H), 3.3 (2H), 2.7 (1H), 2.5 (1H)

4) Synthesis of Compound G 2 g of moisture-controlled glycerol and 40 g of dimethyl carbonate (DMC) were put in a flask, and 2.7 g of thionyl chloride was then slowly added dropwise at 0° C. After a reaction was completed, vacuum distillation was performed to remove both reaction solvent and generated HCl, and 40 g of acetonitrile and 30 g of water were additionally added. Thereafter, 0.5 g of $RuCl_3$ and 6 g of $NaIO_4$, which were dissolved in 20 g of water at 0° C., were slowly added dropwise and stirred. After 30 minutes of reaction, 100 g of t-butyl ether was added and stirred, an organic layer was then separated and extracted with water and ethyl acetate, and, after the extraction, the organic layer was concentrated under reduced pressure to obtain 4-(hydroxymethyl)-1,3,2-dioxathiolane 2,2-dioxide. After 10 g of dimethyl carbonate was put in a flask and 1.5 g of thionyl chloride was slowly added, 2 g of the 4-(hydroxymethyl)-1,3,2-dioxathiolane 2,2-dioxide previously obtained was slowly added at 0° C. After 1 hour, 2 g of 3-hydroxymethyl-1,3-propane sultone, which was dissolved in 5 g of dimethyl carbonate, was slowly added at After a reaction was performed for 3 hours, 50 g of methylene chloride (MC) and water were added to extract an organic layer. After water was removed from the organic layer using $MgSO_4$, the organic layer was dried under reduced pressure to obtain (2,2-dioxido-1,2-oxatholan-5-yl)methyl (2,2-dioxido-1,3,2-dioxathiolan-4-yl) methyl) sulfite (the following Compound G).

[Compound G]

G

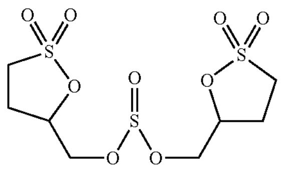

Whether or not the compound was synthesized was confirmed by $^1$H-NMR.

$^1$H-NMR (500 MHz, Bruker, ACN-d3)=5.3 (1H), 5.1 (1H), 4.9 (2H), 4.4~4.1 (2H), 3.87 (1H), 3.75 (1H), 3.4~3.2 (2H), 2.65 (1H), 2.4 (1H)

5) Synthesis of Compound H 2 g of moisture-controlled glycerol and 40 g of dimethyl carbonate (DMC) were put in a flask, and 2.6 g of thionyl chloride was then slowly added dropwise at 0° C. After a reaction was completed, vacuum distillation was performed to remove both reaction solvent and generated HCl, and 3 g of 4-(hydroxymethyl)-1,3,2-dioxathiolane 2-oxide was obtained. 2 g of moisture-controlled glycerol and 20 g of dimethyl carbonate (DMC) were put in another flask, and 5.2 g of thionyl chloride was then slowly added dropwise at 0° C. After a reaction was completed, vacuum distillation was performed to remove both reaction solvent and generated HCl, and 30 g of dimethyl carbonate was additionally added. Thereafter, 3 g of the previously prepared 4-(hydroxymethyl)-1,3,2-dioxathiolane 2-oxide was dissolved in 10 g of dimethyl carbonate and slowly added at 0° C. After 3 hours of reaction, extraction was performed using water and ethyl acetate, and an organic layer was then dried under reduced pressure to obtain bis((2-oxido-1,3,2-dioxathiolan-4-yl)methyl) sulfite (the following Compound H)

[Compound H]

H

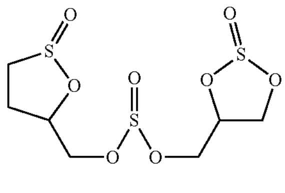

The Compound H is characterized in that it exists in a form in which stereoisomers are mixed in a molar ratio of 6:4 due to a cyclic sulfite structure, and whether or not the compound was synthesized was confirmed by $^1$H-NMR.

$^1$H-NMR (500 MHz, Bruker, $CDCl_3$)=5.15 (1.2H), 4.78 (2H), 4.6 (1.2H), 4.4 (2.8H), 4.2~4.0 (2.8H)

6) Synthesis of Compound I 2 g of moisture-controlled glycerol and 40 g of dimethyl carbonate (DMC) were put in a flask, and 2.7 g of thionyl chloride was then slowly added dropwise at 0° C. After a reaction was completed, vacuum distillation was performed to remove both reaction solvent and generated HCl, and 40 g of acetonitrile and 30 g of water were additionally added. Thereafter, 0.5 g of $RuCl_3$ and 6 g of $NaIO_4$, which were dissolved in 20 g of water at 0° C., were slowly added dropwise and stirred. After 30 minutes of reaction, 100 g of t-butyl ether was added and stirred, an organic layer was then separated and extracted with water and ethyl acetate, and, after the extraction, the organic layer was concentrated under reduced pressure to obtain 4-(hydroxymethyl)-1,3,2-dioxathiolane 2,2-dioxide. After 10 g of dimethyl carbonate was put in a flask and 1.5 g of thionyl chloride was slowly added, 2 g of the 4-(hydroxymethyl)-1,3,2-dioxathiolane 2,2-dioxide previously obtained was slowly added at 0° C. After a reaction was performed for 2 hours, 50 g of methylene chloride (MC) and water were added to extract an organic layer. After water was removed from the organic layer using $MgSO_4$, the organic layer was dried under reduced pressure to obtain bis((2,2-dioxido-1,3,2-dioxathiolan-4-yl))methyl) sulfite (the following Compound I).

[Compound I]

I

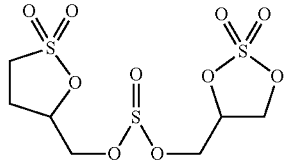

Whether or not the compound was synthesized was confirmed by $^1$H-NMR.

$^1$H-NMR (500 MHz, Bruker, ACN-d3)=5.3 (2H), 4.9~4.8 (4H), 3.8 (4H)

7) Synthesis of Compound X (Comparative Synthesis Example)

50 g of 3-chloro-1,2-propanediol, 60 g of $Na_2SO_3$, and 200 mL of water were put in a flask and heated and stirred at for 7 hours. After the solution was concentrated by vacuum distillation, 300 mL of methanol was added to form a precipitate. The precipitate was vacuum-filtered, then washed with methanol, and vacuum-dried to obtain sodium 2,3-dihydroxypropane sulfonate. 30 g of the dried sodium 2,3-dihydroxypropane sulfonate, 0.5 g of DMF, and 75 mL of toluene were put in a flask, and 48 g of thionyl chloride was slowly dispensed at room temperature. After the dispensing was completed, the reactant was heated at 65° C. for 5 hours. The reactant after the completion of the heating was cooled to room temperature, and 50 mL of MeOH was then added and stirred for 3 hours. The reaction mixture was decompressed to removing a residual solvent, and was then passed through a silica gel column to obtain 2-hydroxy-1,3-propane sultone. 1 g of the prepared 2-hydroxy-1,3-propane sultone was dissolved in 4 mL of acetonitrile, and 0.6 g of pyridine and 0.9 g of thionyl chloride were slowly added dropwise at 0° C. and then reacted at room temperature for 1 hour. Thereafter, 1 g of 2-hydroxy-1,3-propane sultone was slowly added dropwise along with 0.6 g of pyridine, and stirred for 2 hours. After the reaction was completed, an organic layer extracted using ethyl acetate was concentrated. However, since an amount of decomposition products generated during the reaction in this process was large, a yield of Compound X obtained was 40% or less in a concentrate extracted with ethyl acetate, and all the decomposition products were not removed to a water layer so that separation through a silica column (mixture of mobile phase (eluent): ethyl acetate and hexane with a weight ratio of 2:1) was additionally performed again. The additional separation through the silica column was completed to obtain bis(2,2-dioxido-1,2-oxathiolan-4-yl) sulfite (the following Compound X), and a final yield of Compound X was about 20%.

[Compound X]

X

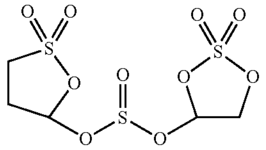

Whether or not the compound was synthesized was confirmed by $^1$H-NMR.

$^1$H-NMR (500 MHz, Bruker, ACN-d3)=5.0 (1H), 4.7 (1H), 4.5 (1H), 3.8 (1H), 3.5 (1H)

8) Synthesis of Compound Y (Comparative Synthesis Example)

3 g of the Compound X obtained by vacuum drying in Synthesis Example 7), 20 g of acetonitrile, and 12 g of water were put in a flask. Thereafter, 0.02 g of $RuCl_3$ and 2.5 g of $NaIO_4$, which were dissolved in 15 g of water at 0° C., were slowly added dropwise and stirred. After 30 minutes of reaction, 50 g of ethyl acetate was added and stirred, an organic layer was then separated and extracted with water and acetyl acetate, and, after the extraction, the organic layer was concentrated under reduced pressure to obtain bis(2,2-dioxido-1,2-oxathiolan-4-yl) sulfate (the following Compound Y). However, it was confirmed that purity of Compound Y was very low due to decomposition products generated in the above process.

In order to obtain Compound Y with higher purity, sulfuryl chloride, instead of thionyl chloride, was used in 1 g of the 2-hydroxy-1,3-propane sultone prepared in Synthesis Example 7), and the same process as in Synthesis Example 7) was performed to obtain Compound Y. However, even in this method, a yield of Compound Y obtained was about 20%.

[Compound Y]

Y

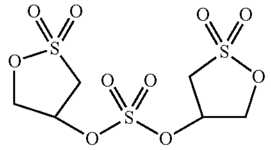

Whether or not the compound was synthesized was confirmed by $^1$H-NMR.

$^1$H-NMR (500 MHz, Bruker, ACN-d3)=5.5 (2H), 5.3 (2H), 5.1 (2H), 3.9 (2H), 3.8 (2H)

9) Synthesis of Compound Z (Comparative Synthesis Example)

5 g of the Compound H obtained by vacuum drying in Synthesis Example 5), 38 g of acetonitrile, and 19 g of water were put in a flask. Thereafter, 0.025 g of $RuCl_3$ and 3.5 g of $NaIO_4$, which were dissolved in 28 g of water at 0° C., were slowly added dropwise and stirred. After 30 minutes of reaction, 90 g of t-butyl ether was added and stirred, and an organic layer was then separated and extracted with water and ethyl acetate. However, since moisture-sensitive bis((2,2-dioxido-1,3,2-dioxathiolan-4-yl)methyl) sulfate (the following compound Z) was all decomposed, it may not be obtained.

Thus, as another synthesis method, sulfuryl chloride, instead of thionyl chloride, was used in 2 g of the 4-(hydroxymethyl)-1,3,2-dioxathiolane 2,2-dioxide prepared in Synthesis Example 6), and the same process as in Synthesis Example 6) was performed to obtain Compound Z. However, even in this method, a yield of Compound Z obtained was about 10%.

[Compound Z]

Z

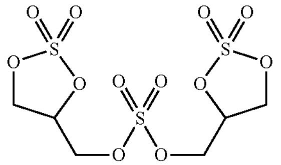

Whether or not the compound was synthesized was confirmed by $^1$H-NMR.

$^1$H-NMR (500 MHz, Bruker, ACN-d3)=5.4 (2H), 4.95~4.8 (4H), 4.6 (4H)

Examples and Comparative Examples

After $LiPF_6$ was dissolved in a non-aqueous organic solvent, in which ethylene carbonate and ethyl methyl carbonate were mixed in a volume ratio of 3:7, such that a concentration of the $LiPF_6$ was 1.0 M, 99 g of the corresponding solution was collected. A non-aqueous electrolyte solution was prepared by adding 1 g of the compound synthesized in the above synthesis example or a conventional additive to the collected solution.

Furthermore, a positive electrode active material (lithium nickel-cobalt-manganese oxide ($Li(Ni_{0.8}Co_{0.1}Mn_{0.1})O_2$)), a conductive agent (carbon black), and a binder (polyvinylidene fluoride) were mixed in a weight ratio of 97.5:1:1.5 and then added to N-methyl-2-pyrrolidone (NMP) to prepare a positive electrode slurry (solid content 60 wt %). A 15 μm thick positive electrode collector (aluminum (Al) thin film) was coated with the positive electrode slurry, dried, and then roll-pressed to prepare a positive electrode. Separately, a negative electrode active material (artificial graphite), a conductive agent (carbon black), and a binder (polyvinylidene fluoride) were mixed in a weight ratio of 96:0.5:3.5 and then added to N-methyl-2-pyrrolidone (NMP) to prepare a negative electrode slurry (solid content 50 wt %). An 8 μm thick negative electrode collector (copper (Cu) thin film) was coated with the negative electrode slurry, dried, and then roll-pressed to prepare a negative electrode. Thereafter, the prepared positive electrode, a porous polyolefin-based separator coated with inorganic material particles ($Al_2O_3$), and the prepared negative electrode were sequentially stacked to prepare an electrode assembly, the assembled electrode assembly was accommodated in a pouch type battery case, and the previously prepared non-aqueous electrolyte solution for a lithium secondary battery was injected thereinto to prepare a pouch type lithium secondary battery.

Types and amounts of additives used in the batteries prepared in the examples and the comparative examples are summarized in Table 1 below.

TABLE 1

| | Additives | Additive amount in the non-aqueous electrolyte solution (wt % ) |
|---|---|---|
| Example 1 | Compound B | 1 |
| Example 2 | Compound A | 1 |
| Example 3 | Compound C | 1 |
| Example 4 | Compound G | 1 |
| Example 5 | Compound H | 1 |
| Example 6 | Compound I | 1 |
| Comparative Example 1 | No additive | 0 |
| Comparative Example 2 | Ethylene sulfate | 1 |
| Comparative Example 3 | 1,3-propane sultone | 1 |
| Comparative Example 4 | Compound X | 1 |
| Comparative Example 5 | Compound Y | 1 |
| Comparative Example 6 | Compound Z | 1 |

Experimental Example 1

Evaluation of High-Temperature Cycle Characteristics of the Batteries

The batteries prepared in the examples and the comparative examples were activated at a constant current (CC) of 0.1 C. Subsequently, each battery was charged at a CC of 0.33 C to 4.2 V under a constant current-constant voltage (CC-CV) charge condition at 25° C. using PESC05-0.5 charge/discharge equipment (manufacturer: PNE SOLUTION Co., Ltd., 5 V, 500 Ma), then subjected to 0.05 C current cut-off, and discharged at 0.33 C to 2.5 V under a constant current condition. The above charging and discharging were defined as one cycle and two cycles were performed. Subsequently, each battery was fully charged at a constant current-constant voltage of 0.33 C/4.2 V, and discharged at 2.5 C for 10 seconds at a state of charge (SOC) of 50% to measure voltages before and after discharging, and initial resistance was calculated using a voltage difference before and after the discharging. Then, after each battery was discharged at a constant current of 0.33 C to 2.5 V, degassing was performed, and each battery was charged at a constant current of 0.33 C to 4.2 V within a voltage operation range of 2.5 V to 4.2 V at 45° C., and subsequently charged at a constant voltage of 4.2 V to terminate charging when the charging current reached 0.05 C. Thereafter, the battery was left standing for 20 minutes, and then discharged at a constant current of 0.33 C to 2.5 V. The above charging and discharging were defined as one cycle and 100 cycles of charging and discharging were repeated.

In this case, capacity after a first cycle and capacity after a 100th cycle were measured using PESC05-0.5 charge/discharge equipment, and a capacity retention was calculated by substituting the capacities into the following [Equation 1].

$$\text{Capacity retention (\%)} = (\text{capacity after 100 cycles/capacity after the first cycle}) \times 100 \quad \text{[Equation 1]}$$

Also, after 100 cycles were performed, each battery was discharged at 2.5 C for 10 seconds at an SOC of 50% to measure voltages before and after discharging, and a resistance value after 100 cycles was calculated using a voltage difference before and after the discharging. A resistance increase rate was calculated by substituting the previously calculated initial resistance value and the resistance value after 100 cycles into the following [Equation 2].

$$\text{Resistance increase rate (\%)} = \{(\text{resistance value after 100 cycles} - \text{initial resistance value})/\text{initial resistance value}\} \times 100 \quad \text{[Equation 2]}$$

Capacity retentions and resistance increase rates calculated for the batteries of each example and comparative example are summarized in Table 2 below.

TABLE 2

| | Capacity retention (%) | Resistance increase rate (%) |
|---|---|---|
| Example 1 | 94 | 13 |
| Example 2 | 95 | 13 |
| Example 3 | 92 | 12 |
| Example 4 | 92 | 12 |
| Example 5 | 93 | 11 |
| Example 6 | 93 | 10 |
| Comparative Example 1 | 78 | 40 |
| Comparative Example 2 | 86 | 35 |
| Comparative Example 3 | 85 | 24 |
| Comparative Example 4 | 90 | 15 |
| Comparative Example 5 | 89 | 15 |
| Comparative Example 6 | 90 | 11 |

As illustrated in Table 2, since Examples 1 to 6 using the non-aqueous electrolyte solution additive of the present invention had higher capacity retentions and lower resistance increase rates than Comparative Example 1 in which no additive was used, it may be confirmed that Examples 1 to 6 had excellent cycle characteristics. Also, since Comparative Examples 2 and 3, in which the conventional non-aqueous electrolyte solution additive was used instead of the additive of the present invention, exhibited lower capacity retentions and higher resistance increase rates than the examples of the present invention, it was confirmed that a battery having particularly excellent cycle characteristics may be prepared when the non-aqueous electrolyte solution additive of the present invention was used.

In addition, Comparative Examples 4 to 6 using Compounds X, Y and Z, which had a structure similar to that of the compound of the present invention, but were not included in the claims of the present invention, as the non-aqueous electrolyte solution additives, respectively, exhibited slightly inferior capacity retentions and resistance increase rates than the examples of the present invention. With respect to the Compounds X, Y and Z, since there was a disadvantage in a synthesis process that they were obtained in a very low yield due to issues, such as not being easily synthesized or decomposed after completion of synthesis, as described in the Synthesis Example section, and also were not better than the compound of the present invention in terms of performance, it may be confirmed that the compound of the present invention was more preferable to be used as the non-aqueous electrolyte solution additive than the Compounds X, Y and Z.

Experimental Example 2

Evaluation of High-Temperature Storage Characteristics of the Batteries

Volume change rate and resistance increase rate after high-temperature storage were measured for the batteries prepared in the examples and the comparative examples by the following methods.

1) Volume Change Rate (%)

After each battery was activated at a constant current of 0.1 C, each battery was charged at a constant current of 0.33 C to 4.2 V under a constant current-constant voltage charge condition at 25° C. using PESC05-0.5 charge/discharge equipment, then subjected to 0.05 C current cut-off, and discharged at 0.33 C to 2.5 V under a constant current condition. The above charging and discharging were defined as one cycle and two cycles were performed. Subsequently, each battery was fully charged at a constant current-constant voltage of 0.33 C/4.2 V, and discharged at 2.5 C for 10 seconds at an SOC of 50% to measure voltages before and after discharging, and initial resistance was calculated using a voltage difference before and after the discharging. Then, after each battery was discharged at a constant current of 0.33 C to 2.5 V, degassing was performed, and an initial volume was measured by putting the previously charged and discharged battery in a bowl filled with water at room temperature using TWD-150DM equipment (manufacturer: Two-pls). Thereafter, the battery was fully charged at a constant current-constant voltage of 0.33 C/4.2 V, and stored at 60° C. for 4 weeks (SOC 100%), and a volume after high-temperature storage was then measured again using the TWD-150DM equipment in the same manner. A volume change rate was calculated by substituting the measured initial volume and volume after high-temperature storage into the following [Equation 3].

[Equation 3]

$$\text{Volume change rate (\%)} = \{(\text{volume after high-temperature storage} - \text{initial volume})/\text{initial volume}\} \times 100$$

2) Resistance Increase Rate (%)

Initial resistance was measured according to the procedure described above, and, after discharging each battery at a constant current of 0.33 C to 2.5 V, degassing was performed, and each battery was charged to 4.2 V. Thereafter, after storage at 60° C. for 4 weeks (SOC 100%), resistance after high-temperature storage was measured while discharging the battery again at 2.5 C for 10 seconds at an SOC of 50%. A resistance increase rate was calculated by substituting the initial resistance value and resistance value after high-temperature storage measured as described above into the following [Equation 4].

[Equation 4]

$$\text{Resistance increase rate (\%)} = \{(\text{resistance value after high-temperature storage} - \text{initial resistance value})/\text{initial resistance value}\} \times 100$$

Volume change rates and resistance increase rates calculated for each battery by the above-described methods are summarized in Table 3 below.

TABLE 3

| | Volume change rate (%) | Resistance increase rate (%) |
|---|---|---|
| Example 1 | 8 | 12 |
| Example 2 | 8 | 12 |
| Example 3 | 10 | 13 |
| Example 4 | 11 | 13 |
| Example 5 | 11 | 12 |
| Example 6 | 14 | 10 |
| Comparative Example 1 | 37 | 45 |
| Comparative Example 2 | 30 | 35 |
| Comparative Example 3 | 25 | 40 |
| Comparative Example 4 | 9 | 14 |
| Comparative Example 5 | 11 | 14 |
| Comparative Example 6 | 16 | 10 |

As illustrated in Table 3, since the batteries of the examples had smaller volume changes due to less gas generation and also had smaller increases in resistance even after high-temperature storage than the batteries of Comparative Examples 1 to 3, it was confirmed that capacity characteristics may be stably maintained.

Also, with respect to the batteries of Comparative Examples 4 to 6, they exhibited performances similar to those of the examples under high-temperature storage conditions, but, as described in Experimental Example 1 above, there were disadvantages in terms of synthesis and storage, and they were disadvantageous in that they were inferior to the examples also in terms of cycle characteristics.

The invention claimed is:

1. A compound represented by Formula 1:

[Formula 1]

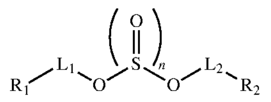

wherein, in Formula 1, n is 1 or 2, $L_1$ and $L_2$ are each independently a direct bond or an unsubstituted or substituted $C_1$ to $C_6$ alkylene group, and $R_1$ and $R_2$ are each independently a substituent represented by Formula 2,

[Formula 2]

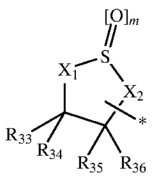

wherein, in Formula 2, m is 1 or 2, $X_1$ and $X_2$ are each independently —O— or —C($R_{31}$)($R_{32}$)—, wherein at least one of $X_1$ or $X_2$ is —O—, and $R_{31}$ to $R_{36}$ are each independently hydrogen, a C1 to C6 alkyl group, —C(═O)—$R_4$, or —$R_5$—O—C(═O)—$R_6$, wherein $R_4$ and $R_6$ are each independently an unsubstituted or substituted C1 to C6 alkyl group, a C2 to C20 alkenyl group, a C2 to C20 alkynyl group, or an unsubstituted or substituted C6 to C20 aryl group, $R_5$ is an unsubstituted or substituted C1 to C6 alkylene group, substituents of $L_1$, $L_2$, $R_4$, $R_5$, and $R_6$ are each independently at least one selected from the group consisting of deuterium, —F, —Cl, —Br, —I, —CN, —$NO_2$, and —$SO_3$, and

* is a position bonded to $L_1$ or $L_2$, wherein, in a case in which both Li and $L_2$ are direct bonds, $R_1$ and $R_2$ are not simultaneously CS-7, and in a case in which n is 2 while both Li and $L_2$ are methylene groups, $R_1$ and $R_2$ are not simultaneously CS-2:

CS-2

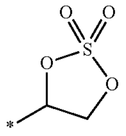

CS-7

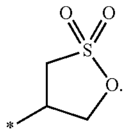

2. The compound of claim 1, wherein $R_1$ and $R_2$ are each independently selected from the group consisting of CS-1 to CS-15:

CS-1

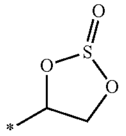

CS-2

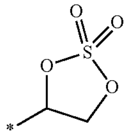

CS-3

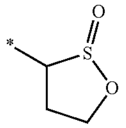

CS-4

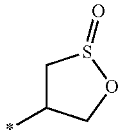

CS-5

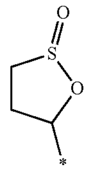

-continued

CS-6

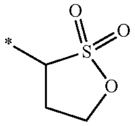

CS-7

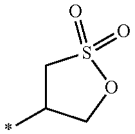

CS-8

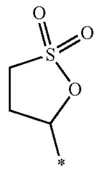

CS-9

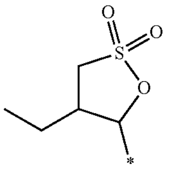

CS-10

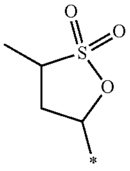

CS-11

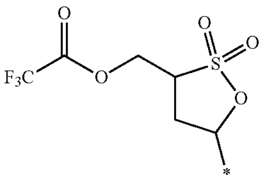

CS-12

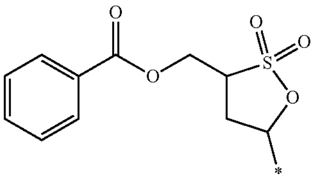

CS-13

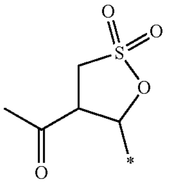

CS-14

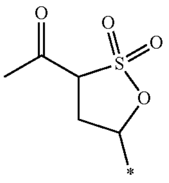

-continued
CS-15
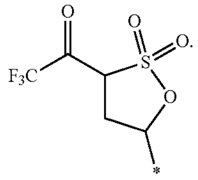
3. The compound of claim 1, wherein $L_1$ and $L_2$ are methylene groups.
4. The compound of claim 2, wherein $R_1$ and $R_2$ are each independently any one selected from the group consisting of CS-1, CS-2, CS-5, CS-8, CS-10, and CS-11.
5. The compound of claim 1, wherein the compound is any one selected from the group consisting of compounds A to C and E to R:
A
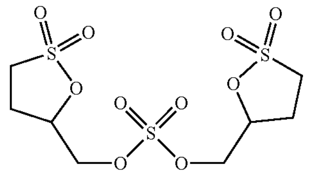
B
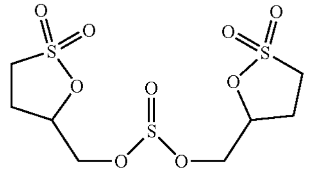
C
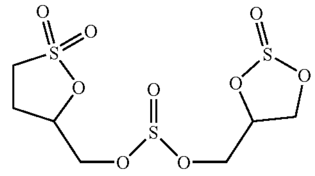
E
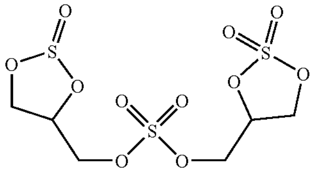
F
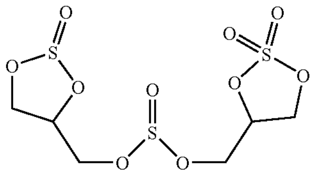
G
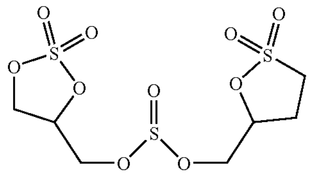
-continued
H
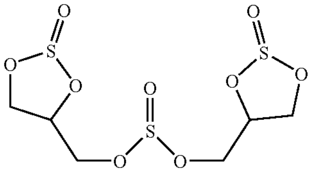
I
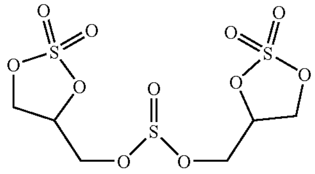
J
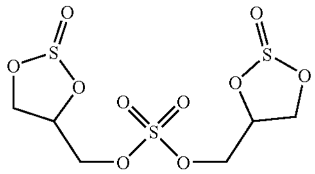
K
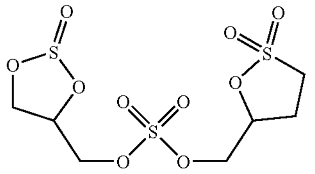
L
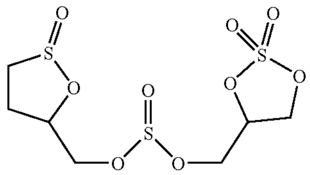
M
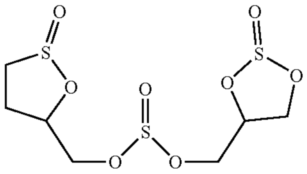
N
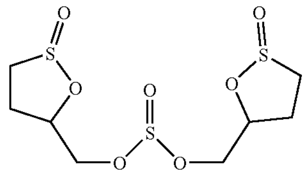
O
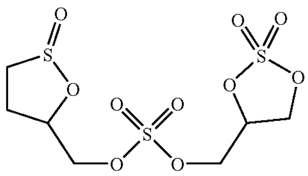

-continued

P

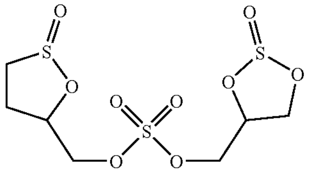

Q

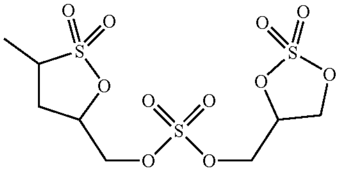

R

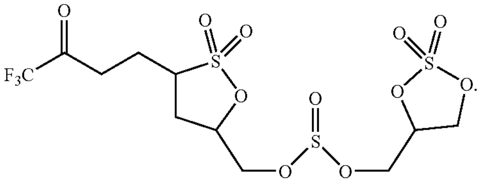

6. A non-aqueous electrolyte solution additive comprising the compound of claim 1.

7. A non-aqueous electrolyte solution comprising:

a lithium salt;

a non-aqueous solvent; and the non-aqueous electrolyte solution additive of claim 6.

8. The non-aqueous electrolyte solution of claim 7, wherein the non-aqueous electrolyte solution additive is included in an amount of 0.01 wt % to 10 wt % based on a total weight of the non-aqueous electrolyte solution.

9. The non-aqueous electrolyte solution of claim 7, wherein the lithium salt is at least one selected from the group consisting of LiCl, LiBr, LiI, $LiBF_4$, $LiClO_4$, $LiB_{10}Cl_{10}$, $LiAlCl_4$, $LiAlO_4$, $LiPF_6$, $LiCF_3SO_3$, $LiCH_3CO_2$, $LiCF_3CO_2$, $LiAsF_6$, $LiSbF_6$, $LiCH_3SO_3$, $LiN(SO_2F)_2$, $LiN(SO_2CF_2CF_3)_2$, and $LiN(SO_2CF_3)_2$.

10. The non-aqueous electrolyte solution of claim 7, wherein the non-aqueous solvent is at least one selected from the group consisting of a cyclic carbonate-based organic solvent, a linear carbonate-based organic solvent, a cyclic ester-based organic solvent, and a linear ester-based organic solvent.

11. A lithium secondary battery comprising:

a positive electrode;

a negative electrode;

a separator; and the non-aqueous electrolyte solution of claim 7.

* * * * *